(12) United States Patent
Feron et al.

(10) Patent No.: US 10,005,894 B2
(45) Date of Patent: Jun. 26, 2018

(54) PLASTICISER COMPOSITIONS COMPRISING GELIFICATION ACCELERATORS BASED ON ESTER(S) OF 1,4 : 3,6-DIANHYDROHEXITOL HAVING LOW MOLAR WEIGHT

(71) Applicants: Thierry Feron, Fouquieres les Bethune (FR); Monique Sobocinski, La Couture (FR); Herve Wyart, Cuinchy (FR); Boris Breitscheidel, Waldsee (FR); Jochen Wagner, Ruppertsweiler (DE)

(72) Inventors: Thierry Feron, Fouquieres les Bethune (FR); Monique Sobocinski, La Couture (FR); Herve Wyart, Cuinchy (FR); Boris Breitscheidel, Waldsee (FR); Jochen Wagner, Ruppertsweiler (DE)

(73) Assignee: ROQUETTE FRERES, Lestrem (FR)

( * ) Notice: Subject to any disclaimer, the term of this patent is extended or adjusted under 35 U.S.C. 154(b) by 435 days.

(21) Appl. No.: 14/397,968

(22) PCT Filed: May 2, 2013

(86) PCT No.: PCT/FR2013/050967
§ 371 (c)(1),
(2) Date: Oct. 30, 2014

(87) PCT Pub. No.: WO2013/164545
PCT Pub. Date: Nov. 7, 2013

(65) Prior Publication Data
US 2015/0125613 A1    May 7, 2015

(30) Foreign Application Priority Data
May 3, 2012 (FR) ..................... 12 54086

(51) Int. Cl.
*C08K 5/15* (2006.01)
*B29C 67/20* (2006.01)
(Continued)

(52) U.S. Cl.
CPC .......... *C08K 5/1535* (2013.01); *C07D 493/04* (2013.01); *C08K 5/0016* (2013.01);
(Continued)

(58) Field of Classification Search
CPC ...... C07D 493/04; C08K 5/0016; C08K 5/10; C08K 5/1535; C08K 5/11; C08K 2201/014; C09D 127/06; C09D 7/1233; C08L 27/06
(Continued)

(56) References Cited

U.S. PATENT DOCUMENTS

| 2002/0019559 A1 | 2/2002 | Brunner et al. |
| 2007/0027242 A1 | 2/2007 | Storzum et al. |

(Continued)

FOREIGN PATENT DOCUMENTS

| CA | 2376742 | 12/2000 |
| DE | 10 2010 002856 | 9/2011 |

(Continued)

OTHER PUBLICATIONS

International Search Report dated Oct. 24, 2013, corresponding to PCT/FR2013/050967.

*Primary Examiner* — William Cheung
(74) *Attorney, Agent, or Firm* — Oliff PLC

(57) ABSTRACT

Disclosed is a composition that can rapidly plasticize polymers, including, in relation to the total mass of (A) and (B): between 0.1 and 99 mass-% of at least one ester of 1,4:3, 6-dianhydrohexitol (A), having a molar mass varying between 255 and 345 g·mol$^{-1}$ and selected from among monoesters and diesters of isosorbide, isomannide and isoi-
(Continued)

dide; and between 1 and 99.9 mass-% of at least one compound (B) having a molar mass greater than 345 g·mol$^{-1}$ and selected from among the esters of 1,4:3,6-dianhydrohexitol, the esters of cyclohexane polycarboxylic acid, the esters of phthalic acid, and glycerol esters. Also disclosed is a method for the production of a plasticized object using constituents (A) and (B), as well as to the use of the ester compound (A) as a polymer gelification accelerator.

27 Claims, 1 Drawing Sheet

(51) Int. Cl.
| | |
|---|---|
| *B28B 1/20* | (2006.01) |
| *C04B 41/50* | (2006.01) |
| *C08K 5/1535* | (2006.01) |
| *C07D 493/04* | (2006.01) |
| *C08K 5/00* | (2006.01) |
| *C08K 5/10* | (2006.01) |
| *C08K 5/11* | (2006.01) |
| *C08K 5/12* | (2006.01) |
| *C09D 127/06* | (2006.01) |

(52) U.S. Cl.
CPC ............... *C08K 5/10* (2013.01); *C08K 5/11* (2013.01); *C08K 5/12* (2013.01); *C09D 7/63* (2018.01); *C09D 127/06* (2013.01); *C08K 2201/014* (2013.01)

(58) Field of Classification Search
USPC ............ 427/385.1; 106/287.2; 264/175, 311; 524/109
See application file for complete search history.

(56) References Cited

U.S. PATENT DOCUMENTS

2009/0301348 A1  12/2009  Grass et al.
2012/0220507 A1*  8/2012  Grass .................. C07D 307/68
                                                        508/309

FOREIGN PATENT DOCUMENTS

| WO | 99/32427 | 7/1999 |
| WO | 99/45060 | 9/1999 |
| WO | 00/78853 | 12/2000 |

* cited by examiner

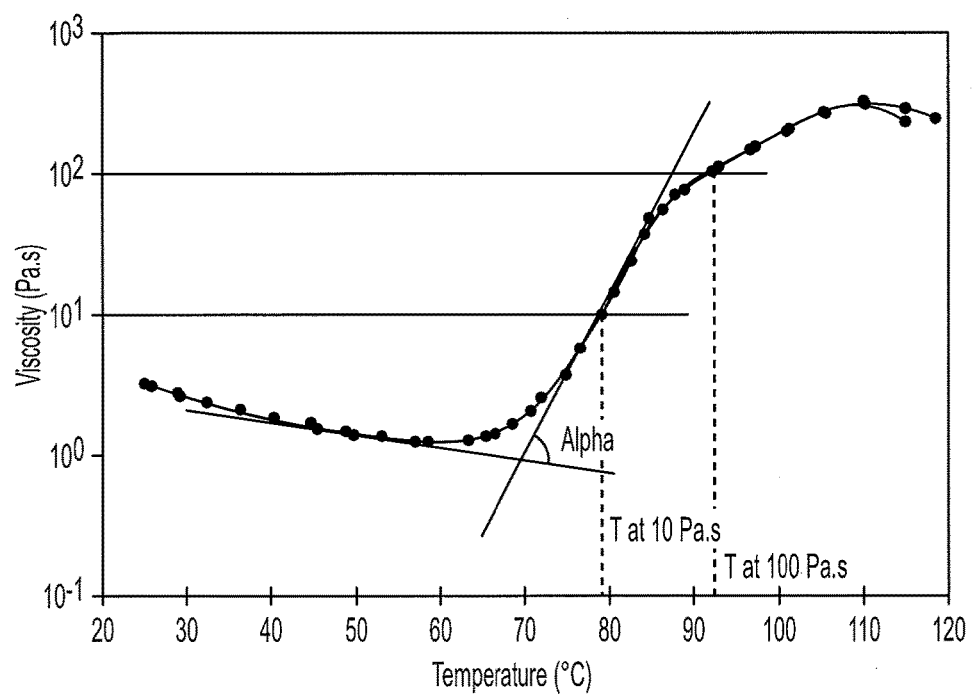

PLASTICISER COMPOSITIONS COMPRISING GELIFICATION ACCELERATORS BASED ON ESTER(S) OF 1,4 : 3,6-DIANHYDROHEXITOL HAVING LOW MOLAR WEIGHT

The present application is a National Stage of PCT International Application Serial Number PCT/FR2013/050967, filed May 2, 2013, and claims priority under 35 U.S.C. § 119 of France, U.S. patent application Ser. No. 12/540,86, filed May 3, 2012, the disclosures of which are incorporated by reference herein.

FIELD OF THE INVENTION

The subject matter of the invention is a composition, of use as plasticizer for polymers, comprising at least one 1,4:3,6-dianhydrohexitol ester and a second compound having the role of plasticizer. Another aspect of the invention relates to the use of this 1,4:3,6-dianhydrohexitol ester as accelerator of the gelling of polymers.

STATE OF THE ART

Due to their many advantages, the use of synthetic polymers has become widespread in numerous applications since the last century.

However, these polymers can exhibit disadvantages, such as, in particular, their mechanical properties, which may be insufficient for some uses. For example, they may exhibit a very low elongation at break at ambient temperature or be not very impact resistant.

Furthermore, it may be necessary to modify the behavior of these polymers in the molten phase, in particular in order to be able to employ them in transformation processes of coating type or also in calendering. In other words, it is necessary for the polymer to have exceeded its melting point or also its gelling temperature and thus for the polymer to exhibit, in this gelled state, a viscosity suited to the shaping process in order to be able to be correctly transformed.

In order to be able to use them in more varied applications, it is also necessary to modify the properties of these polymers, for example in order to render them more flexible or more impact resistant or also to allow them to have a softer appearance.

For this, these polymers can be blended with "plasticizers".

"Plasticizer" is understood to mean any product which, when it is blended in a sufficient amount with a polymer, has the role of decreasing the glass transition temperature of said polymer.

By decreasing the glass transition temperature of the polymer, the flexibility of the latter is increased and the mechanical properties of this plasticized polymer are modified. Thus, by adding a plasticizer to a polymer composition, a decrease in the Young's modulus, a decrease in the breaking stress and/or an increase in the strain at break are generally observed.

These modified properties of the polymer then allow it to be used in more varied applications, for example in flexible sheets or films.

During the process of processing the plastic, the plasticizers are generally blended with the polymer, which makes possible the decrease in the softening temperature of the polymer.

This mixing can be carried out by different processing processes.

In the case of polyvinyl chlorides (PVCs), for example, the polymer can be transformed into an object by various techniques for the transformation of thermoplastic materials and in particular by extrusion, by calendering or also by coating via a process of plastisol type.

In order to obtain this thermoplastic blend, the PVC is blended with the plasticizer by introducing energy into this system in the form of temperature and of mechanical energy. In the case of extrusion or kneading, this blending is carried out in a closed system. In the case of a blending on rolls, this blending is carried out in an open system. The polymer can subsequently be shaped, for example by thermoforming or calendering processes. Generally, a dry blending stage is carried out before the stage of thermomechanical blending.

According to the plastisol process, blending is generally carried out to form a PVC paste; this paste is subsequently shaped by a coating or molding stage in which the paste is heated in an oven in order to form the part.

Whatever the process, it is necessary for the polymer to be correctly melted or gelled in order to be able to be satisfactorily shaped and thus to see to it that the object formed at the end of the process has good properties.

For all these processes for producing thermoplastic blends starting from PVC, use is generally made of plasticizers of the family of the phthalic esters. They are still to this day very generally dioctyl phthalate or diisononyl phthalate. These plasticizers are very effective for the plasticizing of polymers and are readily available on the market for a relatively low cost.

However, due to the problems of toxicity of the phthalates, other plasticizers have also been developed in recent years, such as cyclohexanepolycarboxylic acid and its derivatives, which have formed the subject of the patent applications WO 00/78853 and WO 99/32427. Mention may be made, by way of example, of the diisononyl ester of 1,2-cyclohexanedicarboxylic acid sold by BASF under the Hexamoll® trademark.

Mention may also be made, as other plasticizer, of glycerol ester derivatives, such as Grindsted®, obtained from glycerol and castor oil and sold by Danisco. These plasticizers exhibit the advantage of being obtained from biosourced products.

The use of 1,4:3,6-dianhydrohexitol derivatives as plasticizers for polymers has already been described in the document WO 99/45060. These derivatives do not exhibit the problems of toxicity of the phthalates. In addition, these plasticizers exhibit the advantage of being at least partially biosourced.

The mechanical properties of the polymers plasticized with these derivatives are excellent and similar to those obtained with plasticizers of phthalate type.

In context of its research studies, the applicant company has found that some of these compounds exhibit the disadvantage of plasticizing the polymers relatively slowly, which necessitates the use of greater thermomechanical energy for the shaping of the polymer. This also involves implies long transformation times and thus a loss in productivity.

This same problem is also observed when the phthalic esters, cyclohexanepolycarboxylic acid derivatives and glycerol ester derivatives already mentioned are used as plasticizers. To respond to this problem of slow rate of plasticization, use is generally made, in the processing process, of gelling accelerators, also known as plasticizing accelerators, well known to a person skilled in the art under the term of fast fuser. These compounds are generally used in combination with the plasticizers in the processing process.

Without being committed to any one theory, the applicant company explains the effect of acceleration of the gelling by the fact that the substance rapidly penetrates into the polymer and comes in between the chains of this polymer. The network of the polymer molecules is thus very rapidly rendered "looser", which makes possible rapid gelling and easier introduction of the plasticizer between the chains of the polymer, which has the effect of more rapidly producing a plasticized polymer.

The consequence for the process is that the polymer can be transformed faster and/or with less thermomechanical energy.

Mention may be made, as example of gelling accelerator which is already known, of diisobutyl phthalate (DIBP), triacetin or the commercial products Jayflex™ MB 10 (isodecyl monobenzoate), sold by Exxon Mobil, or Santicizer® 9500 (2-ethylhexyl monobenzoate), sold by Ferro.

One disadvantage of these accelerators is that their use generally brings about a relatively large release of volatile organic compounds (hereinafter VOCs) during the processing.

This release is all the greater in processes using an open blending system, such as calendering processes or plastisol coating processes, as large amounts of volatile materials are emitted during the manufacture of products according to these processing forms.

Furthermore, it has been possible to observe that the gelling accelerators generally used have a tendency, during the use of the object formed from the plastic, to "migrate" out of the object formed. It is also said that the product exudes. This results in accelerated UV and thermal aging of the plastic formed, which has the consequence of diminishing the mechanical properties thereof. The surface of this object thus gives off pollutants, which is even more problematic when it is a packaging and when the contents are contaminated by these substances or also when the objects are placed inside buildings, particularly in crèches or hospitals.

The document US 2007/0027242 describes, in the example, a blend of phthalates of use as plasticizer, this blend comprising esters of phthalic acid and of saturated alcohols comprising 7 carbon atoms (with a molar mass equal to 362 g·mol$^{-1}$) and also esters of phthalic acid and of saturated alcohols comprising 10 carbon atoms (with a molar mass equal to 446 g·mol$^{-1}$). The ester manufactured from the saturated alcohols comprising 7 carbon atoms is used as a gelling accelerator. The advantage put forward for this composition is that it is relatively nonvolatile, in comparison with compositions comprising, as gelling accelerator, the commonest, for example dibutyl phthalate or diisobutyl phthalate. However, this plasticizing blend is not completely satisfactory in terms of rate of plasticization. Furthermore, the applicant company has even been able to confirm (see examples) that the C$_7$ phthalic ester is not very effective at all as gelling accelerator when it is combined with other types of plasticizers than phthalates, for example with a 1,4:3,6-dianhydrohexitol diester or with an ester of cyclohexanepolycarboxylic acid.

It thus remains necessary to find novel processes, using specific compounds, which make it possible to solve as best as possible all of these problems and which constitute an excellent compromise in the properties already described.

Finally, some of these plasticizers, in particular some 1,4:3,6-dianhydrohexitol derivatives, can exhibit freezing points of approximately 0° C. During the storage of these plasticizers, which can take place outside and thus at very low negative temperatures, this freezing point may be problematic, indeed even completely unacceptable, as the plasticizer is then difficult to handle.

In order to make possible the storage of these plasticizers even under unfavorable weather conditions, it is thus necessary to find compositions, capable of plasticizing polymers, which remain liquid, even at temperatures reaching −10° C., indeed even −15° C.

Thus, in addition to novel processes, it is often necessary to find novel compositions which make it possible to solve as best as possible all of the abovementioned problems.

SUMMARY OF THE INVENTION

The applicant company has had the credit of finding this specific composition which makes it possible to very efficiently plasticize polymers, while making it possible to respond to the various problems described above.

This plasticizing composition comprises a compound (A) which acts as a gelling accelerator and a compound (B) which acts as a plasticizer.

A subject matter of the invention is thus a composition comprising:

from 0.1% to 99% by weight of at least one 1,4:3,6-dianhydrohexitol ester (A), the molar mass of which ranges from 255 to 345 g·mol$^{-1}$, which is chosen from isosorbide, isomannide and isoidide monoesters and diesters;

from 1% to 99.9% by weight of at least one compound (B), the molar mass of which is greater than 345 g·mol$^{-1}$, chosen from:

esters of cyclohexanepolycarboxylic acid;

esters of phthalic acid;

glycerol esters.

The composition according to the invention, according to some alternative forms, additionally has the advantage of exhibiting a better resistance to cold than the plasticizer compositions already known. This is particularly true for the compositions where the compound (B) is a 1,4:3,6-dianhydrohexitol ester.

The invention also relates to a process for the manufacture of an object based on a plasticized polymer composition comprising a polymer (C) and the composition comprising (A) and (B) according to the invention. This process comprises the following stages:

a stage of selecting the ester (A), the compound (B) and the polymer (C);

a stage of introducing the constituents (A), (B) and (C) into a mixer system, (A) and (B) being introduced in the proportions as defined in the composition of the invention;

a stage of mixing the constituents (A), (B) and (C);

a stage of heating this blend;

a stage of shaping the blend into the form of an object;

finally, a stage of recovering said object comprising the plasticized polymer composition; it being possible for the stage of introducing the constituents (A), (B) and (C) into the mixer to be carried out separately or via a blend of constituents, and simultaneously or sequentially; it being possible for the mixing and heating stages to be carried out simultaneously or sequentially.

The invention will now be described in detail in the continuation of the description.

BRIEF DESCRIPTION OF THE FIGURES

The FIGURE indicates the change in the viscosity as a function of the temperature of a polymer paste comprising a polyvinyl chloride and a gelling accelerator.

DETAILED DESCRIPTION OF THE INVENTION

The process and the composition according to the invention both use the compounds (A) and (B), which will now be described in detail.

The compound (A) is a 1,4:3,6-dianhydrohexitol ester (A), the molar mass of which ranges from 255 to 345 g·mol$^{-1}$, chosen from isosorbide, isomannide or isoidide monoesters and diesters.

The ester groups of the ester (A) are chosen in order for the molar mass (A) to range from 255 to 345 g·mol$^{-1}$. This ester group can result from a carboxylic acid, that is to say be capable of being obtained by reaction of a carboxylic acid with an alcohol functional group of the 1,4:3,6-dianhydrohexitol. For example, if the acid is valeric acid, the ester group is a valerate group. Advantageously, the 1,4:3,6-dianhydrohexitol ester groups are groups comprising from 2 to 8 carbon atoms, that is to say that the acid reacting with the 1,4:3,6-dianhydrohexitol comprises from 2 to 8 carbon atoms.

Preferably, the ester group of the ester (A) is an alkyl group, that is to say that the ester is obtained by reaction of 1,4:3,6-dianhydrohexitol with one or more saturated monocarboxylic acids. The alkyl group can be a cycloalkyl, linear alkyl or branched alkyl group. Preferably, the alkyl group is linear or branched, very preferably linear.

This ester (A) can be chosen from 1,4:3,6-dianhydrohexitol dipropionates, 1,4:3,6-dianhydrohexitol dibutyrates, 1,4:3,6-dianhydrohexitol diisobutyrates, 1,4:3,6-dianhydrohexitol divalerates, 1,4:3,6-dianhydrohexitol diisovalerates, 1,4:3,6-dianhydrohexitol dihexanoates, 1,4:3,6-dianhydrohexitol propionates butyrates, 1,4:3,6-dianhydrohexitol propionates isobutyrates, 1,4:3,6-dianhydrohexitol propionates valerates, 1,4:3,6-dianhydrohexitol propionates isovalerates, 1,4:3,6-dianhydrohexitol propionates hexanoates, 1,4:3,6-dianhydrohexitol butyrates isobutyrates, 1,4:3,6-dianhydrohexitol butyrates valerates, 1,4:3,6-dianhydrohexitol butyrates isovalerates, 1,4:3,6-dianhydrohexitol butyrates hexanoates, 1,4:3,6-dianhydrohexitol isobutyrates valerates, 1,4:3,6-dianhydrohexitol isobutyrates isovalerates, 1,4:3,6-dianhydrohexitol isobutyrates hexanoates, 1,4:3,6-dianhydrohexitol valerates hexanoates and 1,4:3,6-dianhydrohexitol isovalerates hexanoates.

Very preferably, the ester (A) is a 1,4:3,6-dianhydrohexitol divalerate or a 1,4:3,6-dianhydrohexitol dihexanoate, preferably a 1,4:3,6-dianhydrohexitol divalerate.

Preferably, the 1,4:3,6-dianhydrohexitol ester (A) is an isosorbide ester.

These esters, the ester groups of which are alkyl groups, are particularly effective, in particular in their preferred alternative forms. As isomannide, isoidide and isosorbide can be obtained respectively from mannitol, iditol and sorbitol, which are themselves obtained from starch, the 1,4:3,6-dianhydrohexitol esters of use in the invention additionally exhibit the advantage of being partially biosourced, indeed even completely biosourced if use is made of an acid which is also biosourced.

The composition according to the invention comprises at least one ester (A), that is to say that it can comprise a blend of esters (A) described above.

These esters are known and can be obtained by an esterification reaction of 1,4:3,6-dianhydrohexitol with at least one carboxylic acid. This carboxylic acid can be ethanoic acid, propionic acid, butyric acid, isobutyric acid, valeric acid, isovaleric acid, hexanoic acid, heptanoic acid and octanoic acid. The synthesis of these esters is presented, for example, in the document WO 99/45060 already mentioned.

According to the invention, the compound (B) is a compound, the molar mass of which is greater than 345 g·mol$^{-1}$, which is chosen from:

1,4:3,6-dianhydrohexitol esters chosen from isosorbide, isomannide and isoidide monoesters and diesters, the 1,4:3,6-dianhydrohexitol ester groups of which are groups comprising from 1 to 24 carbon atoms, preferably groups comprising 6 to 12 carbon atoms;

esters of cyclohexanepolycarboxylic acid;

esters of phthalic acid;

glycerol esters.

The compounds (B) have to be chosen in order to have a molar mass of greater than 345 g·mol$^{-1}$. The molar mass of the compound (B) can range, for example, from 350 to 1000 g·mol$^{-1}$, preferably from 390 to 600 g·mol$^{-1}$.

The composition according to the invention comprises at least one compound (B), that is to say that it can comprise a blend of compounds (B) of use in the invention.

Advantageously, the compound (B) is a 1,4:3,6-dianhydrohexitol diester or an ester of cyclohexanepolycarboxylic acid.

According to the preferred alternative form where the compound (B) is a 1,4:3,6-dianhydrohexitol diester, the 1,4:3,6-dianhydrohexitol ester (B) is very preferably an isosorbide ester.

Preferably, the ester group of the ester (B) is an alkyl group, that is to say that the ester is obtained by reaction of 1,4:3,6-dianhydrohexitol with one or more saturated monocarboxylic acids. The alkyl group can be a cycloalkyl, linear alkyl or branched alkyl group. Preferably, the alkyl group is linear or branched, very preferably linear.

The ester group or groups of the 1,4:3,6-dianhydrohexitol ester comprise from 1 to 24 carbon atoms, that is to say that the acid reacting with the 1,4:3,6-dianhydrohexitol comprises from 1 to 24 carbon atoms. Advantageously, the ester group or groups comprise from 4 to 16 carbon atoms, preferably comprise from 5 to 11, for example from 6 to 12, very preferably from 7 to 10.

This ester (B) can be chosen from 1,4:3,6-dianhydrohexitol diheptanoates, 1,4:3,6-dianhydrohexitol dioctanoates, 1,4:3,6-dianhydrohexitol dinonanoates, 1,4:3,6-dianhydrohexitol didecanoates, 1,4:3,6-dianhydrohexitol diundecanoates, 1,4:3,6-dianhydrohexitol didodecanoates, 1,4:3,6-dianhydrohexitol heptanoates hexanoates, 1,4:3,6-dianhydrohexitol heptanoates octanoates, 1,4:3,6-dianhydrohexitol heptanoates nonanoates, 1,4:3,6-dianhydrohexitol heptanoates decanoates, 1,4:3,6-dianhydrohexitol heptanoates undecanoates, 1,4:3,6-dianhydrohexitol heptanoates dodecanoates, 1,4:3,6-dianhydrohexitol octanoates valerates, 1,4:3,6-dianhydrohexitol octanoates isovalerates, 1,4:3,6-dianhydrohexitol octanoates hexanoates, 1,4:3,6-dianhydrohexitol octanoates nonanoates, 1,4:3,6-dianhydrohexitol octanoates decanoates, 1,4:3,6-dianhydrohexitol octanoates undecanoates, 1,4:3,6-dianhydrohexitol octanoates dodecanoates, 1,4:3,6- dianhydrohexitol nonanoates butyrates, 1,4:3,6-dianhydrohexitol nonanoates valerates, 1,4:3,6-dianhydrohexitol nonanoates isovalerates, 1,4:3,6-dianhydrohexitol nonanoates hexanoates, 1,4:3,6-dianhydrohexitol nonanoates decanoates, 1,4:3,6-dianhydrohexitol nonanoates undecanoates, 1,4:3,6-dianhydrohexitol nonanoates dodecanoates, 1,4:3,6-dianhydrohexitol decanoates butyrates, 1,4:3,6-dianhydrohexitol decanoates valerates, 1,4:3,6-dianhydrohexitol decanoates isovalerates, 1,4:3,6-dianhydrohexitol decanoates hexanoates, 1,4:3,6-dianhydrohexitol decanoates undecanoates, 1,4:3,6-dianhydrohexitol decanoates dodecanoates, 1,4:3,6-dianhydrohexitol undecanoates butyrates, 1,4:3,6-dianhydrohexitol undecanoates valerates, 1,4:3,6-dianhydrohexitol undecanoates isovalerates, 1,4:3, 6-dianhydrohexitol undecanoates hexanoates and 1,4:3,6-dianhydrohexitol undecanoates dodecanoates.

As for the ester (A), this ester (B) is capable of being produced by an esterification reaction of 1,4:3,6-dianhydrohexitol with a carboxylic acid or a blend of these acids.

Mention may be made, as example of carboxylic acid, of butyric acid, isobutyric acid, valeric acid, isovaleric acid, hexanoic acid, heptanoic acid, octanoic acid, nonanoic acid, decanoic acid, undecanoic acid, dodecanoic acid, tridecylic acid, myristic acid, pentadecylic acid or palmitic acid.

These compounds (B) can be obtained by carrying out an esterification reaction between the 1,4:3,6-dianhydrohexitol and one or different carboxylic acids. In the case where just one of the two alcohol functional groups of the diol has reacted by esterification, the ester is a monoester. It is a diester in the case where both the alcohol functional groups of the diol have reacted in an esterification reaction. The 1,4:3,6-dianhydrohexitol ester is preferably a diester. According to this embodiment, the 1,4:3,6-dianhydrohexitol diester can comprise different ester groups, that is to say that the diester is obtained with two different acids.

The synthesis of the 1,4:3,6-dianhydrohexitol esters is also described in the document WO 99/45060 already mentioned.

The esters of cyclohexanepolycarboxylic acid are known and are described, for example, in the application WO 99/32427 or the application WO 00/78853. Provided that their molar mass exceeds 345 g·mol$^{-1}$, the esters of cyclohexanepolycarboxylic acid mentioned from page 5, line 14, to page 12, line 9, of the application WO 00/78853 can be used as compound (B).

It is preferable to use esters of cyclohexanedicarboxylic acid and in particular the diesters of this acid. Use is advantageously made of the esters of 1,2-cyclohexanedicarboxylic acid. Preferably, the esters of cyclohexanepolycarboxylic acid are diisononyl esters, such as, for example, the diisononyl ester of 1,2-cyclohexanedicarboxylic acid. The latter is sold by BASF under the Hexamol® trademark. These compounds can be obtained in a known way by reacting cyclohexanepolycarboxylic acid with an alcohol or by hydrogenation of phthalates.

Esters of phthalic acid (or phthalates) are also well known plasticizers. By way of example, they can be dioctyl phthalate or diisononyl phthalate. These compounds can be obtained by reacting phthalic acid with an alcohol.

Glycerol esters are known and can be, for example, the glycerol esters sold by Danisco under the Grinsted® trademark. These compounds (B) can be obtained by carrying out an esterification reaction between glycerol and a carboxylic acid, for example one of the carboxylic acids already mentioned for the manufacture of the 1,4:3,6-dianhydrohexitol esters.

It is specified that the carboxylic acid or acids reacting with 1,4:3,6-dianhydrohexitol or glycerol are chosen in order for the compound (B) to exhibit a molar mass of greater than 345 g·mol$^{-1}$. Likewise, it is specified that the alcohol or alcohols reacting with cyclohexanepolycarboxylic acid or phthalic acid are chosen in order for the ester compound (B) to exhibit a molar mass of greater than 345 g·mol$^{-1}$.

Advantageously, the composition according to the invention comprises, with respect to the total weight of the composition, at least 50% of (A) and (B), preferably at least 80%, more preferably at least 90% and more preferably still at least 95%. The composition according to the invention very advantageously consists of (A) and (B).

According to the process and the composition of the invention, the amount by weight of (A) advantageously ranges from 0.1% to 99%, with respect to the total weight of (A) and (B), advantageously from 0.5% to 50%.

The advantages of the process and of the composition according to the invention are particularly marked when the amount by weight of (A) is within the range extending from 1% to 25%, with respect to the total weight of (A) and (B), advantageously ranging from 2% to 20%, for example ranging from 4% to 19%.

The composition according to the invention, which is a plasticizing composition capable of rapidly plasticizing polymers, has in addition the advantage of exhibiting a very good resistance to cold.

Another subject matter of the invention is the use of the composition according to the invention to plasticize a polymer (C).

Another subject matter of the invention is a process for plasticizing a polymer, characterized in that it comprises a stage which consists in blending said polymer with the composition according to the invention.

Another subject matter of the invention is a process for reducing the glass transition temperature of a polymer, characterized in that it comprises a stage which consists in blending said polymer with the composition according to the invention.

The blending is preferably carried out using thermomechanical energy, such as to intimately blend the composition and the polymer.

The polymer to be plasticized (C) can be chosen from vinyl polymers, such as polyvinyl chloride, polyurethanes, polyesters, cellulose polymers, starches, acrylic polymers, polyacetates and polyamides and the blends of these polymers. Advantageously, it is vinyl polymer, preferably polyvinyl chloride. Polyvinyl chloride is understood to mean, according to the present invention, vinyl chloride homopolymers or copolymers comprising vinyl chloride, for example vinyl acetate/vinyl chloride copolymers.

The polymer thus obtained is a polymer plasticized by the composition comprising (A) and (B). For a person skilled in the art, this means that the polymer (C) and the composition comprising (A) and (B) are intimately blended. The constituents (A) and (B), which are naturally in the liquid state, are introduced between the chains of the solid polymer and this results in a plasticized polymer composed of a solid phase.

Prior to the blending thereof with (A) and (B), the polymer (C) can be in any form, for example in the form of granules or of powder.

Another subject matter of the invention is a polymer paste comprising a blend of a polymer powder and of the composition according to the invention. This paste is generally referred to as plastisol and makes it possible to form objects by the processes described hereinafter. Preferably, the mean diameter of the particles of powder is between 1 and 30 µm, for example between 1 and 20 µm. In the case of polyvinyl chloride, powders of this type can be obtained by preparing the PVC by emulsion or microsuspension. This paste is generally obtained by mechanical blending, preferably without heating, of the polymer (C) powder with (A) and (B).

During the blending, the polymer (C) disintegrates and the mean diameter of the polymer particles decreases. In the plastisol, the particles generally have a mean diameter of approximately 0.5 to 30 µm, for example of 0.5 to 20 µm. The blends thus obtained are known as plastisols, which are more or less fluid according to the amounts of (A), (B) and (C). Conventionally, plastisols are prepared in turbine-type rapid mixers, planetary mixers or slow mixers which are horizontal Z-blade planetary mixers.

The constituents (A), (B) and (C) are advantageously in proportions by weight such that the sum of (A) and (B) ranges from 1 to 900 parts per 100 parts of polymer (C), advantageously from 5 to 150 parts, preferably from 10 to 120 parts, of (A) and (B). They can be introduced into the mixer system by any appropriate means, such as feed hopper, or manually.

In the case of the polymer paste, it is preferable for the amounts of plasticizer to range from 30 to 80 parts of (A) and (B) per 100 parts of polymer powder.

In the plasticized polymer composition, use may also be made, in addition to the constituents (A), (B) and (C), of optional additives. These additives can be chosen from stabilizers, including UV stabilizers, fillers, dyes, pigments, blowing agents, emulsifiers, viscosity-lowering agents other than (A), thickeners, mold-release agents, matting agents, adhesion agents, antistatic agents, fungicidal agents and odoriferous agents. The amounts of each additive are chosen in order to introduce the desired properties during the processing of the process or for the object finally obtained. These additives can be introduced into the composition directly or as a blend. The amount of optional additive generally ranges from 1 to 600 parts per 100 parts of polymer (C), generally from 2 to 80 parts.

It is possible, still according to the invention, to manufacture objects comprising the plasticized polymer composition by using a process for the manufacture of an object based on a plasticized polymer composition comprising a polymer (C) and the constituents (A) and (B) as are used in the composition of the invention.

This process comprises:
a stage of selecting the ester (A), the compound (B) and the polymer (C);
a stage of introducing the constituents (A), (B) and (C) into a mixer system, the amounts of (A) and (B) being introduced in the proportions as defined in the composition of the invention described above;
a stage of mixing the constituents (A), (B) and (C);
a stage of heating this blend;
a stage of shaping the blend into the form of an object;
finally, a stage of recovering said object comprising the plasticized polymer composition;
it being possible for the stage of introducing the constituents (A), (B) and (C) into the mixer to be carried out separately or via a blend of constituents, and simultaneously or sequentially; and
it being possible for the mixing and heating stages to be carried out simultaneously or sequentially.

Advantageously, the constituents (A) and (B) are introduced into the mixer system via the composition according to the invention.

According to a first alternative form of the process of the invention, the process comprises a stage of thermomechanical blending.

According to this first alternative form, the stage of thermomechanical blending is carried out in a mixer system which is a mixer for thermoplastics. This mixer can be chosen from kneaders, Buss mixers, open mills and extruders.

The constituents (A) and (B) can be introduced in the form of one or more masterbatches.

The stage of thermomechanical mixing is carried out at a temperature suited to the temperature for transformation of the polymer (C). By way of example, the temperature of the blend during the thermomechanical blending is preferably between 60 and 200° C. for PVC.

For a thermomechanical blending, use may be made of a polymer under any type of form.

According to this first alternative form, a preliminary stage of dry blending the constituents (A), (B) and (C) is advantageously carried out before the thermomechanical blending. This dry blending can be carried out in a simple mechanical mixer.

According to this alternative form, the process according to the invention is particularly advantageous when the shaping stage is a calendering stage. This is because the calendering is carried out in a calender, which is an open system. In point of fact, the process is particularly advantageous in this case as the amounts of VOCs given off during the process are particularly low in comparison with those given off in the processes using other gelling accelerators than the compounds (A).

The object can also advantageously be shaped by other methods, in particular by injection molding, extrusion injection molding, molding, extrusion molding, thermoforming, extrusion forming, extrusion sheathing or extrusion blow-molding. Use may also be made of coextrusion techniques in order to form multilayer objects.

According to a second alternative form, use is made, in order to form the object according to the invention, of a process of plastisol type with the polymer paste described above.

In this type of process, the shaping stage is generally a stage of coating, of dipping, of slushing or of rotational molding of the polymer paste, which makes it possible to form a preformed object.

The heating stage of the process is a stage of curing said preformed object, which can take place during the stage of shaping the preformed object (this is the case, for example, of the dipping, slushing or rotational molding) or take place after the stage of shaping the preformed object (this is the case, for example, of the coating). This curing stage can be carried out at a temperature of between 60 and 300° C., for example between 100 and 250° C. It can be carried out under air or under a controlled atmosphere, for example under an inert atmosphere.

The stage of shaping the object is preferably a stage of coating the polymer paste onto the support, this coating being carried out before the stage of curing said coated support. The coating stage can be carried out on a textile support, synthetic polymer or paper.

The coating can be carried out using any coating head, for example using a scraper or a roll.

This coating can, according to a first alternative subform, be a "coating on support" coating as described above or, according to a second alternative subform, be a "support-free coating". In the latter case, the support of the coated support can be detached after curing and the process additionally comprises a subsequent stage of separation of the support in order to form a film or a sheet of plasticized polymer. Such a support can be made of silicone-treated paper.

The curing stage is generally carried out in an oven, for example a tunnel oven.

Another subject matter of the invention is an object comprising the plasticized polymer composition which is capable of being obtained by the process of the invention.

The object comprising the plasticized polymer composition can be any type of object, such as a film, a sheet, a granule, a floor covering, a wall covering, a plastic-coated fabric, in particular artificial leather, for example for footwear, for fine leather goods or for furniture, a tarpaulin, a liner, for example for a swimming pool, a blind, a flexible container, an item of clothing, a medical product, a glove, a boot, a seal, a protective coating, a dummy for a shop window, a toy, for example a ball or a doll, a pipe, profiled elements, in particular window profiled elements, or motor vehicle parts, such as instrument panel, seat, tank or headrest. These parts can be foamed or expanded parts, that is to say comprising air cells. They can also, on the contrary, be solid parts.

Furthermore, the applicant company has also discovered that some 1,4:3,6-dianhydrohexitol ester compounds have the ability to accelerate the plasticizing or the gelling of polymers, while giving off small amounts of VOCs during the processing process.

The invention thus also relates to the use of the esters (A) described above as gelling accelerators in a polymer shaping process. Generally, it is considered that a compound is a gelling accelerator when it has the ability to melt the polymer more rapidly than a plasticizer of diisononyl phthalate (DINP) type. A simple way of measuring it is to form a first blend from 60 parts of compound and 100 parts of a polymer powder and to measure the development of the viscosity of this blend as a function of the temperature using a plate-plate rheometer. In order to measure this change in the viscosity, this blend can be deposited in a rheometer and a shear rate of 10 $s^{-1}$ with a rotational angle of 2° can be applied. Before the measurement, the blend is conditioned for 10 minutes by applying the abovementioned shear rate and subsequently the temperature in the rheometer is increased, for example at a rate of 5.7 K/min, and the viscosity of this first blend is measured until the polymer melts and its viscosity reaches 10 $Pa \cdot s^{-1}$. This test is repeated, in which a second blend identical to the first blend is used, apart from the difference that DINP replaces the test compound. If the first blend comprising the test compound reaches a viscosity of 10 $Pa \cdot s^{-1}$ at a lower temperature than the second blend, then the compound tested is a gelling accelerator.

After formation of the object, another advantage of these accelerators is that a low exudation is observed during use of the object, in comparison with objects comprising the gelling accelerators already known.

Another subject matter of the invention is a process for accelerating the gelling of a blend comprising a polymer and a plasticizer, characterized in that a 1,4:3,6-dianhydrohexitol ester (A) according to the invention, the molar mass of which ranges from 255 to 345 $g \cdot mol^{-1}$, chosen from isosorbide, isomannide and isoidide monoesters and diesters, is added to said blend.

Specific embodiments of the invention will now be described in detail in the examples which follow. It is specified that these specific examples do not in any way limit the present invention.

EXAMPLES

Example 1: Volatility Properties of the Gelling Accelerators

The gelling accelerators used in the example which follows are:
IDV (gelling accelerator according to the invention): isosorbide divalerate, exhibiting a molar mass of 314 $g \cdot mol^{-1}$;
DBP: dibutyl phthalate;
Jayflex™ MB 10: isodecyl monobenzoate (Exxon Mobil);
Santicizer® 9500: 2-ethylhexyl monobenzoate (Ferro).
Preparation and Tests:

The volatility of the gelling accelerators is determined by difference in weight after a defined residence time in a ventilated oven. 5 g of the test product are weighed out exactly in a crystallizing dish. The crystallizing dish is subsequently placed inside the oven at 180° C. for 30 min. Once this time has elapsed, the crystallizing dish is placed in a desiccator until it is cooled. The crystallizing dish is subsequently weighed and the volatility is then calculated according to the following formula:

(starting plasticizer weight−plasticizer weight after residence in the oven)×100/starting plasticizer weight.

The results obtained with regard to the products tested appear in table 1.

TABLE 1

| Plasticizers | Volatility in % |
|---|---|
| IDV (accelerator according to the invention) | 11 |
| Santicizer ® 9500 | 93 |
| DBP | 24 |
| Jayflex ™ MB 10 | 40 |

The tests show that IDV differs markedly from the other gelling accelerators in a much lower volatility. Thus, it is not the level of volatility which is normally encountered for these compounds of low molar mass. It will thus furthermore have the effect of releasing less VOCs during the shaping process and also during the use thereof.

The applicant company has been able to find, with surprise, that, despite this very low volatility, the product has excellent properties of accelerating the gelling of polymers, as is shown in the following example 2.

Example 2: Properties of Accelerating the Gelling of Polymers

The gelling accelerators used are:
IDV (gelling accelerator according to the invention): isosorbide divalerate
Citrofol® B2: tributyl acetylcitrate (Jungbunzlauer)
Jayflex™ MB 10: isodecyl monobenzoate (Exxon Mobil)
DHP: phthalic diester of a saturated alcohol comprising 7 carbon atoms (accelerator used in the document US 2007/0027242).
The plastisol formulations are prepared using the following products:
Solvin® 372 NF: PVC emulsion; 100 parts
Gelling accelerator: 60 parts
Lankromark® LZB 753: heat stabilizer based on Ba/Zn; 2 parts Preparation of the PVC:

2.1 Evaluation of the Gelling Accelerators

The gelling accelerator is introduced into a plastic container containing the PVC at the same time as the heat stabilizer. The preparation is subsequently stirred using a motor equipped with a stirrer blade of Rayneri type, at slow speed. The blending speed is then increased to 2000 rev/min for 150 seconds. The preparation is subsequently placed in a desiccator under vacuum in order to remove the air bubbles therefrom. The PVC paste thus obtained is also known as plastisol.

The paste is subsequently used to measure the development of its viscosity as a function of the temperature using a rheometer of Physica MCR rheometer type. In order to measure this change in the viscosity, a drop of the paste is placed on a plate with a diameter of 50 mm and an angle of 2°. The shear rate chosen is 10 s$^{-1}$ and the temperature gradient is 5.7 K/min. Before the measurement, the paste is conditioned for 10 minutes by applying the abovementioned shear rate and subsequently the temperature gradient is applied. The measurement is halted when the temperature reaches 150° C. or if the torque resulting from the measurement reaches a value which is too high for the measurement system.

The results of the change in the viscosity as a function of the temperature according to this measurement protocol are presented in table 2 below, through the expression of an angle "Alpha", an angle determined from the tangent to the curve of change of the viscosity as a function of the temperature (cf. the FIGURE).

The temperature for which the PVC paste reached a viscosity equal to 10 Pa·s (denoted "T at 10 Pa·s", cf. the FIGURE) is also recorded as a relevant criterion for evaluation of the effectiveness of the gelling accelerators.

TABLE 2

| Accelerator | Alpha in degrees | T at 10 Pa · s in ° C. |
|---|---|---|
| IDV (accelerator according to the invention) | 79 | 67 |
| Citrofol ® B2 | 72 | 83 |
| Jayflex ™ MB 10 | 71 | 76 |
| DHP | 73 | 83 |

It may be noted that, the higher the value of the angle Alpha, the greater the rate of increase in the viscosity of the PVC paste and thus the greater the effectiveness of the accelerator. The angle Alpha observed for IDV is significantly higher than those obtained with the products Citrofol® B2 and Jayflex™ MB 10. According to these tests, DHP for its part is an even poorer gelling accelerator than the products Citrofol® B2 and Jayflex™ MB 10. IDV is thus an excellent gelling accelerator for PVC and more effective than many commercial gelling accelerators.

Furthermore, the temperature necessary for the PVC paste to reach a viscosity of 10 Pa·s is the lowest with IDV. This reinforces and confirms a greater rapidity of the accelerator according to the invention since the temperature necessary to initiate the gelling is lower by 9 to 16° C. with regard to the commercial gelling accelerators tested. Thus, a significant saving in energy can be achieved during the gelling of the plastisols by using the gelling accelerator according to the invention.

2.2 Evaluation of Plasticizing Compositions

The applicant company has also carried out, using this same protocol, tests using plasticizing compositions according to the invention and comparative compositions, blending a plasticizer (P) with a gelling accelerator (GA).

The plasticizers (P):
IDE: isosorbide octanoic diester having a molar mass of 398 g·mol$^{-1}$
DINP: diisononyl phthalate (Sigma Aldrich)
Hexamoll® DINCH: diisononyl cyclohexane (BASF)

The gelling accelerators (GA):
IDV: accelerator used in the invention: isosorbide divalerate
DBP: dibutyl phthalate;
DHP: phthalic diester of a saturated alcohol comprising 7 carbon atoms (accelerator used in the document US 2007/0027242);
Jayflex™ MB 10: isodecyl monobenzoate (Exxon Mobil)
Santicizer® 9500: 2-ethylhexyl monobenzoate (Ferro)

The plastisol formulations are produced using the following products:
Solvin® 372 NF: PVC emulsion; 100 parts
Plasticizing composition: 60 parts with variable ratios of plasticizer and of gelling accelerator (P/GA)
Baerostab® NT 319P: heat stabilizer based on Ba/Zn; 1.5 parts
Baerostab LSA®: costabilizer based on epoxidized soybean oil; 2 parts The protocol for the preparation of the PVC pastes is identical to that described above.

The temperature for which the PVC paste has reached:
a viscosity equal to 10 Pa·s (denoted "T at 10 Pa·s"),
a viscosity equal to 100 Pa·s (denoted "T at 100 Pa·s", cf. the FIGURE),
is observed, as a relevant criterion for evaluation of the effectiveness of the plasticizing compositions.

The results given in table 3 are obtained with PVCs comprising IDE and DINCH as sole plasticizer:

TABLE 3

| Plasticizer P | T at 10 Pa · s (° C.) | T at 100 Pa · s (° C.) |
|---|---|---|
| IDE | 79 | 90 |
| DINCH | 95 | 126 |

The results obtained for the different pastes based on PVC and on plasticizing compositions are presented in table 4 below.

TABLE 4

| | | T at 10 Pa · s (° C.) | | T at 100 Pa · s (° C.) | |
|---|---|---|---|---|---|
| P | GA | Ratio 95/5 (P/GA) | Ratio 80/20 (P/GA) | Ratio 95/5 (P/GA) | Ratio 80/20 (P/GA) |
| IDE | IDV | 77 | 74 | 87 | 82 |
| IDE | Santicizer ® 9500 | 78 | 75 | 90 | 83 |
| IDE | DBP | 76 | 72 | 86 | 79 |
| IDE | Jayflex ™ MB 10 | 78 | 77 | 90 | 89 |
| IDE | DHP | 79 | 78 | 90 | 89 |
| DINCH | IDV | Not measured | 85 | Not measured | 101 |
| DINCH | Jayflex ™ MB 10 | Not measured | 92 | Not measured | 122 |
| DINCH | Citrofol ® B2 | Not measured | 90 | Not measured | 100 |
| DINCH | DHP | Not measured | 93 | Not measured | 120 |
| DINP | IDV | 80 | 76 | 89 | 83 |
| DINP | DHP | 82 | 79 | 93 | 87 |

Thus, on comparing the latter results with those of table 3, the tests show that, from the addition of 5 parts of IDV, the gelling temperature is reduced, whatever the plasticizer used. This decrease becomes more significant as the amount of gelling accelerator increases.

Furthermore, IDV clearly appears here as a viscosity accelerator as effective as, indeed even more effective than, the accelerators already known. It is in particular more effective than DHP, whatever the plasticizer used (IDE, DINCH or DINP).

DHP does not behave as a gelling accelerator when it is used in a plasticizing blend with IDE or DINCH, as is shown by the gelling temperatures of the polymer, which are respectively very close to the gelling temperature of the polymer plasticized with IDE alone and DINCH alone.

Example 3: Evaluation of the Mechanical Properties

Plasticized PVC formulations according to the invention and comparative formulations are produced using the following products:
PVC Marvylan® 57102: 100 parts
Stabilizer Baerostab® NT 319P (Ca/Zn powder): 1.5 parts
Costabilizer Baerostab® LSA (epoxidized soybean oil): 2 parts
Plasticizer and gelling accelerator: 34 parts The pressed test specimens intended for the characterization of the mechanical properties are prepared in several stages.

In a first step, it is necessary to plasticize PVC powder with the plasticizing composition in a planetary mixer of Planetmix 500 type (Thermo Fisher) equipped with a Polystat in order to ensure regulation of the temperature. This mixer is filled with PVC, the heat stabilizer and the heat costabilizer. The plasticizing composition is subsequently incorporated over the entire surface of the PVC powder when the temperature reaches 85° C. The preparation is thus blended for 8 min.

In a second step, plasticized PVC plaques are prepared using a press of Carver type and a 30×30 cm mold made of mirror polished stainless steel provided with a frame with a thickness of 2 mm and with a mirror polished stainless steel cover. Thus, the frame is placed inside the mold and 180 g of plasticized PVC powder are poured therein. The powder is distributed uniformly and is covered with the cover. The assembly is placed on the plate of the press and the programming is carried out of a clamping force of 18 000 kg for 2 min and then cooling down to 40° C. to 50° C. The PVC plaque thus obtained is then removed from the mold.

Finally, in a final stage, 10 test specimens of 5A type are cut out, using a hollow punch, from the plasticized PVC plaques obtained as described above (dimension of the test specimens=length: 25 mm; width: 4 mm; thickness: 2 mm).

These test specimens are subsequently characterized in traction on a tensile/compression testing machine of Lloyd LR5K plus model type with the following parameters: rate of progression: 50 mm/min; cell: 5 kN; the prestress is reset to zero once the test specimen is in place and once the jaws are gripping.

Once the test is complete, the Young's modulus and the percentage of elongation at break are recorded.

All of the mechanical properties modified by the plasticization, namely the modulus of rigidity (Young's modulus) and the degree of elongation at break, are presented in table 5 below for each composition tested.

TABLE 5

| Plasticizer | Young's modulus (MPa) | Elongation at break (%) |
|---|---|---|
| IDE | 5.0 | 591 |
| IDE/IDV (ratio 80/20) | 4.6 | 612 |
| IDE/Santicizer® 9500 (ratio 80/20) | 4.6 | 568 |
| IDE/Jayflex™ MB 10 (ratio 80/20) | 5.7 | 549 |
| IDE/DBP (ratio 80/20) | 4.9 | 589 |
| DINP alone | 6.2 | 551 |
| DINP/IDV (ratio 80/20) | 6.5 | 529 |
| DINCH alone | 6.7 | 520 |
| DINCH/IDV (ratio 80/20) | 6.7 | 490 |

These tests show that the addition of a commercial gelling accelerator, such as DBP or Santicizer® 9500, only slightly modifies the mechanical properties of a plasticized PVC with IDE as plasticizer.

In the same way, the addition of IDV as gelling accelerator does not modify the mechanical properties of the plasticized PVCs. The addition of IDV at a content of 20% to the IDE/IDV plasticizing composition brings about a very slight fall in modulus of 8% and an increase in the elongation at break of 3.5%, which is also slight. These results are comparable to those obtained with DBP. The same phenomenon could be observed with other plasticizers than IDE (DINCH, DINP). The addition of IDV thus does not bring about a deterioration in the mechanical properties of the PVC obtained. Thus, the use of IDV makes it possible to retain the mechanical properties of the plasticized polymers.

Example 4: Effect on the Properties of Migration of the Plasticizing Composition Preparation of the Tests:
PVC test specimens (40×40 mm, thickness 2 mm) are cut out from a PVC plaque as produced in example 3. They are conditioned at 20° C./65% RH for 72 h. The same is done with absorbent supports (10×10 cm (100 cm$^2$) Canson blotting paper). The test specimens and the absorbent supports are then weighed on a precision balance. The plasticized PVC test specimens are subsequently placed between the two absorbent supports, at the center of these. This assembly is positioned between two glass plates and a weight of 5 kg is placed on top. The combination is placed in a ventilated oven at 70° C. for 4 weeks. After 4 weeks, the test specimens are again conditioned at 20° C./65% RH for 2 days. Finally, they are reweighed in order to determine the degree of migration from the test specimen as follows:

(test specimen weight before oven−test specimen weight after oven)×100/test specimen weight before oven.

TABLE 6

| Plasticizer | Degree of migration (%) |
|---|---|
| IDE | 0.29 |
| IDE/IDV (ratio 97/3) | 0.35 |
| IDE/IDV (ratio 95/5) | 0.35 |
| IDE/IDV (ratio 90/10) | 0.31 |
| IDE/IDV (ratio 85/15) | 0.30 |
| IDE/IDV (ratio 80/20) | 0.29 |

One of the essential criteria for any plasticized polymer is the degree of migration from the plasticizing composition used. This is because this has to be minimal if it is desired to retain the properties of the material over time.

In a ratio of 80/20, a degree of migration is observed which is equivalent to the degree observed for IDE; there is thus, at this ratio, no migration added by the IDV as a blend with the IDE. This is surprising as, in view of the fact that it behaves as a gelling accelerator, a significant impact on the migration might have been expected. This is because the degrees of migration strongly increase when conventional commercial gelling accelerators are used, as is shown by the other results obtained and combined in the following table 7.

TABLE 7

| Plasticizer | Degree of migration (%) | Percentage of increase in the degree of migration with respect to the plasticizer alone |
|---|---|---|
| IDE alone | 0.29 | — |
| IDE/IDV (ratio 80/20) | 0.29 | 0% |
| IDE/Santicizer ® 9500 (ratio 80/20) | 2.58 | 790% |
| IDE/Jayflex ™ MB10 (ratio 80/20) | 0.59 | 103% |
| IDE/DBP (ratio 80/20) | 1.15 | 296% |
| IDE/DHP (ratio 80/20) | 0.85 | 193% |
| DINP alone | 0.13 | — |
| DINP/IDV (ratio 80/20) | 0.20 | 54% |
| DINCH alone | 0.19 | — |
| DINCH/IDV (ratio 80/20) | 0.22 | 16% |

These tests show that the migration added by the other gelling accelerators can be very high. Specifically, the migration increases by approximately 300% with DBP, approximately 200% with DHP and indeed even approximately 800% with Santicizer® 9500.

It can also be shown that the gelling accelerator according to the invention also does not migrate very much with other plasticizers than IDE (DINP, DINCH).

This shows that the composition according to the invention has the ability, after blending in the polymer, to migrate less with respect to the comparative compositions using known gelling accelerators, in particular those described in the document US 2007/0027242.

Example 5: Improvement in the Low-Temperature Freezing Point of the Plasticizer

Tests have been carried out in order to evaluate the impact of the addition of IDV to the plasticizer IDE.

The change in the viscosity of the plasticizer as a function of the temperature is measured using a rheometer of Physica MCR rheometer type. In order to measure this change in the viscosity, a drop of the plasticizer is placed on a plate with a diameter of 50 mm and an angle of 1° (CP 50-1 geometry) for a measurement of the viscous and elastic moduli as a function of the temperature. The temperature gradient is 2° C./min, the temperature sweep is from 20° C. to −50° C., the oscillation frequency is 1 hertz and the strain is from 1% to 0.1%. The freezing point measured corresponds to the change in state temperature of the product subjected to the test and corresponds to the crossing of the viscous and elastic moduli.

The measurements of the freezing point are taken up in table 8.

TABLE 8

| Plasticizer | Freezing point (° C.) |
|---|---|
| IDE | −7 |
| IDE/IDV (ratio 90/10) | −11 |
| IDE/IDV (ratio 80/20) | −14 |

The addition of IDV has a significant impact on the freezing point of the IDE.

Plasticizers for PVC are liquid products intended to be stored in storage canisters. The latter may be set up outside the production buildings where they are employed. It is therefore necessary for the plasticizers to have relatively low freezing points (temperature at which the product begins to change in state in order to pass from the liquid state to the frozen state). In the opposite case, they have to be insulated, indeed even thermally regulated.

With the addition of IDV, it is therefore no longer necessary in some cases to use insulated or thermally regulated storage systems for the storage of the plasticizer.

The invention claimed is:

1. A composition comprising A and B, wherein A ranges from 0.5% to 50% of a total weight of A and B, and A is of at least one 1,4:3,6-dianhydrohexitol ester with a molecular weight of 255 to 345 g/mol, selected from a group consisting of isosorbide, isomannide and isoidide monoesters and diesters; and B is from 50% to 95.5% by weight with a molecular weight greater than 345 g/mol, selected from a group consisting of esters of cyclohexanepolycarboxylic acid, esters of phthalic acid, esters of 1,4:3,6-dianhydrohexitol and glycerol esters.

2. The composition as claimed in claim 1, in which the 1,4:3,6-dianhydrohexitol ester is an ester of an acid of from 2 to 8 carbon atoms, with the proviso that when the at least one ester is a diester of the same acid, the acid contains from 2 to 5 carbon atoms.

3. The composition as claimed in claim 1, in which the 1,4:3,6-dianhydrohexitol ester A is an alkyl ester.

4. The composition as claimed in claim 1, in which A is selected from a group consisting of 1,4:3,6-dianhydrohexitol dipropionates, 1,4:3,6-dianhydrohexitol dibutyrates, 1,4:3,6-dianhydrohexitol diisobutyrates, 1,4:3,6-dianhydrohexitol divalerates, 1,4:3,6-dianhydrohexitol diisovalerates, 1,4:3,6-dianhydrohexitol dihexanoates, 1,4:3,6-dianhydrohexitol propionates butyrates, 1,4:3,6-dianhydrohexitol propionates isobutyrates, 1,4:3,6-dianhydrohexitol propionates valerates, 1,4:3,6-dianhydrohexitol propionates isovalerates, 1,4:3,6-dianhydrohexitol propionates hexanoates, 1,4:3,6-dianhydrohexitol butyrates isobutyrates, 1,4:3,6-dianhydrohexitol butyrates valerates, 1,4:3,6-dianhydrohexitol butyrates isovalerates, 1,4:3,6-dianhydrohexitol butyrates hexanoates, 1,4:3,6-dianhydrohexitol isobutyrates valerates, 1,4:3,6-dianhydrohexitol isobutyrates isovalerates, 1,4:3,6-dianhydrohexitol isobutyrates hexanoates, 1,4:3,6-dianhydrohexitol valerates hexanoates and 1,4:3,6-dianhydrohexitol isovalerates hexanoates.

5. The composition as claimed in claim 1, in which A is a 1,4:3,6-dianhydrohexitol divalerate or a 1,4:3,6-dianhydrohexitol dihexanoate.

6. The composition as claimed in claim 1, in which A is an isosorbide ester.

7. The composition as claimed in claim 1, in which B is an ester of cyclohexanepolycarboxylic acid.

8. The composition as claimed in claim 1, in which B is an isosorbide diester with a at least one $C_6$-$C_{12}$ alkyl group.

9. A polymer paste comprising a blend of a polymer powder and the composition as claimed in claim 1.

10. A method for plasticizing a polymer comprising blending the composition as claimed in claim 1 with the polymer.

11. The paste as claimed in claim 9, in which the polymer is selected from a group consisting of polyvinyl chloride, polyurethanes, polyesters, cellulose polymers, starches, acrylic polymers, polyacetates, polyamides, and mixtures thereof.

12. The method as claimed in claim 10, in which the polymer is selected from a group consisting of polyvinyl chloride, polyurethanes, polyesters, cellulose polymers, starches, acrylic polymers, polyacetates, polyamides, and mixtures thereof.

13. A process for manufacturing an object comprising a polymer C and the composition comprising A and B as claimed in claim 1, said process comprising:
    selecting A, B and the polymer C;
    introducing A, B and the polymer C into a mixer system, wherein A accelerates gelling and is added at a wt. % of between 1% to 25% of a total weight of A and B;
    mixing A, B and the polymer C to provide a blend;
    heating the blend;
    shaping the blend into a form of an object; and
    recovering the object,
    wherein A, B and the polymer C are introduced into a mixer system separately or via a mixture thereof, and simultaneously or sequentially; and
    the mixing and heating are carried out simultaneously or sequentially.

14. The process as claimed in claim 13, in which the mixing is thermomechanical mixing, and the mixer system is a mixer for thermoplastics, selected from a group consisting of a kneader, a Buss mixer, an open mill, and an extruder.

15. The process as claimed in claim 13, in which the shaping is a calendering stage.

16. The process as claimed in claim 13, wherein
    the mixing A, B and the polymer C to provide a blend is to provide a polymer paste;
    the heating provides curing of the blend;
    the shaping the blend into a form of an object comprises coating, dipping, slushing or rotationally molding this polymer paste to form a preformed object.

17. The process as claimed in claim 16, wherein the shaping is coating on a support.

18. The process as claimed in claim 17, wherein the polymer is selected from a group consisting of polyvinyl chloride, polyurethanes, polyesters, cellulose polymers, starches, acrylic polymers, polyacetates, polyamides, and mixtures thereof.

19. The process as claimed in claim 13, wherein the sum of A and B ranges from 1 to 900 parts per 100 parts of polymer C by weight.

20. A method for accelerating the gelling of a blend comprising a polymer and a plasticizer, comprising adding to the blend ranges from 1% to 25% by weight of a 1,4:3,6-dianhydrohexitol ester relative to a total weight of said plasticizer and said ester, the molar mass of said ester which ranges from 255 to 345 g·mol$^{-1}$, selected from a group consisting of isosorbide, isomannide and isoidide monoesters and diesters.

21. The composition as claimed in claim 1, in which A ranges from 1% to 25% of the total weight of A and B.

22. The composition as claimed in claim 21, in which A ranges from 4% to 19% of the total weight of A and B.

23. The composition as claimed in claim 1, in which A ranges from 2% to 20% of the total weight of A and B.

24. The paste as claimed in claim 9, in which the polymer is polyvinyl chloride.

25. The method as claimed in claim 10, in which the polymer is polyvinyl chloride.

26. The process as claimed in claim 17, wherein the polymer is polyvinyl chloride.

27. The process as claimed in claim 13, wherein the sum of A and B ranges from 10 to 120 parts per 100 parts of polymer C by weight.

* * * * *